US010178971B2

(12) United States Patent
Wang et al.

(10) Patent No.: US 10,178,971 B2
(45) Date of Patent: Jan. 15, 2019

(54) ACQUIRING CERVICAL IMAGES (71) Applicant: KONINKLIJKE PHILIPS N.V., Eindhoven (NL)

(72) Inventors: Lu Wang, Eindhoven (NL); Subhendu Seth, Bangalore (IN); Pallavi Vajinepalli, Bangalore (IN); Vipin Gupta, Bangalore (IN); Payal Keswarpu, Bangalore (IN); Sarif Kumar Naik, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/784,961

(22) PCT Filed: Apr. 10, 2014

(86) PCT No.: PCT/EP2014/057241
§ 371 (c)(1),
(2) Date: Oct. 16, 2015

(87) PCT Pub. No.: WO2014/170199
PCT Pub. Date: Oct. 23, 2014

(65) Prior Publication Data
US 2016/0058362 A1 Mar. 3, 2016

(30) Foreign Application Priority Data

Apr. 18, 2013 (EP) ..................................... 13164281

(51) Int. Cl.
*A61B 5/00* (2006.01)
*A61B 1/00* (2006.01)
(Continued)

(52) U.S. Cl.
CPC .......... *A61B 5/4331* (2013.01); *A61B 1/0005* (2013.01); *A61B 1/00009* (2013.01);
(Continued)

(58) Field of Classification Search
CPC ............................ A61B 5/0084; A61B 5/0059
See application file for complete search history.

(56) References Cited

U.S. PATENT DOCUMENTS 6,603,552 B1\* 8/2003 Cline ................... A61B 5/0059
356/39
2007/0088833 A1 4/2007 Yang et al.
(Continued)

FOREIGN PATENT DOCUMENTS

EP 1790277 A1 5/2007
JP 2010099139 A 5/2010
(Continued)

OTHER PUBLICATIONS

Nakappan et a, Methodology of a Real-Time Quality Control for the Multispectral Digital Colposcope (MDS), Gynecologic Oncology, vol. 107, Oct. 1, 2007, pp. S215-S222.
(Continued)

*Primary Examiner* — Hien Nguyen (57) ABSTRACT

The invention provides a system (100) for acquiring cervical images which comprises an image acquisition subsystem (120) for acquiring cervical images (122) of a cervical region of a patient during a colposcopy procedure, and a display subsystem (160) for displaying the cervical images on a display (060) by providing image data (162) of the cervical images to the display. According to the invention, the image acquisition subsystem (120) is arranged for, when operating in an interval mode, acquiring the cervical images (122) at predetermined time intervals to obtain a time-series of cervical images showing changes in the cervical region over time, and reporting a progress of said acquiring to the display subsystem. Moreover, the display subsystem (160) is arranged for establishing a progress indicator (400-416) on the display by generating indicator data (164) and providing the indicator data to the display (060), the progress indicator
(Continued)

providing visual feedback on the progress of said acquiring to a user. Accordingly, the user is provided with visual feedback on a status of the acquiring of the cervical images. In particular, the progress indicator avoids that the user experiences a loss of control or confusion.

12 Claims, 3 Drawing Sheets

(51) Int. Cl.
    *A61B 1/303*     (2006.01)
    *A61B 1/04*     (2006.01)

(52) U.S. Cl.
    CPC ...... *A61B 1/00045* (2013.01); *A61B 1/00055* (2013.01); *A61B 1/04* (2013.01); *A61B 1/303* (2013.01); *A61B 5/0084* (2013.01); *A61B 5/7221* (2013.01); *A61B 5/743* (2013.01); *A61B 5/7425* (2013.01)

(56) References Cited

U.S. PATENT DOCUMENTS

| | | | |
|---|---|---|---|
| 2007/0268280 A1* | 11/2007 | Fujita | A61B 1/00045 345/204 |
| 2008/0226147 A1 | 9/2008 | Gu et al. | |
| 2009/0187071 A1 | 7/2009 | Kim | |
| 2010/0086286 A1* | 4/2010 | Lee | A61B 1/0005 386/201 |
| 2011/0274338 A1* | 11/2011 | Park | G06K 9/6284 382/133 |
| 2012/0188332 A1* | 7/2012 | Yamaguchi | H04N 1/215 348/36 |
| 2012/0238810 A1 | 9/2012 | Kobayashi et al. | |
| 2013/0100265 A1* | 4/2013 | Suzuki | A61B 1/00045 348/74 |
| 2013/0281845 A1* | 10/2013 | Luiken | A61B 5/0071 600/431 |
| 2015/0248223 A1 | 9/2015 | Krupnik et al. | |

FOREIGN PATENT DOCUMENTS

| | | |
|---|---|---|
| WO | 2012001560 A2 | 1/2012 |
| WO | 2012123881 A2 | 9/2012 |
| WO | 2013150419 A1 | 10/2013 |

OTHER PUBLICATIONS

Skladnev et al, "Digital Imaging", CME Journal of Gynecologic Oncology, vol. 10, 2005, pp. 127-132.

* cited by examiner

| INTERVAL MODE | [9 /15], 60% |
| | 3:01 / 5:00 |

Fig. 6

ACQUIRING CERVICAL IMAGES

CROSS-REFERENCE TO PRIOR APPLICATIONS

This application is the U.S. National Phase application under 35 U.S.C. § 371 of International Application No. PCT/EP2014/057241, filed on Apr. 10, 2014, which claims the benefit European Patent Application No. EP13164281.1, filed on Apr. 18, 2013. These applications are hereby incorporated by reference herein.

FIELD OF THE INVENTION

The invention relates to a system and a method for acquiring cervical images of a cervical region of a patient during a colposcopy procedure. The invention further relates to a workstation and an imaging system comprising the system. The invention further relates to a computer program product for causing a processor system to perform the method.

Colposcopy is a medical diagnostic procedure for examining the cervix and adjoining regions for cervical cancer and other medical conditions. Cervical cancer is a leading cause of cancer for women in India and other developing nations. A colposcopy typically comprises applying a chemical solution to the cervical region to improve the visibility of lesions in the cervix area. Examples of such chemical solutions are staining solutions comprising acetic acid or iodine, or cleansing solutions such as saline solutions. After application of the chemical solution, one or more cervical images of the cervical region are acquired, e.g., for medical diagnostic purposes or documentation purposes. Acquiring such cervical images typically involves focusing and positioning a camera a short distance from the patient's vagina and using a speculum to separate its walls slightly apart.

BACKGROUND OF THE INVENTION

The application of an acetic acid solution, and in particular a 3-5% acetic acid solution, is known to accentuate the visual appearance of lesions and other abnormalities in the vascular pattern of the tissue in the cervical region. Said accentuation is typically maximal at about 2 minutes after the application of the acetic acid solution. Moreover, the accentuation fades away at about 5 minutes after the application of the acetic acid solution.

It is desirable to acquire images of the gradual changes in the cervical region as a result of the application of the acetic acid solution. For that purpose, the Goldway SLC-2000B video colposcope may be used as described on a webpage consulted on Apr. 4, 2013 at the web address: http://www.healthcare.philips.com/main/products/goldway/gynecology-solutions/slc-2000b-video-colposcope/. The Goldway SLC-2000B video colposcope provides a so-termed image labeling mode which enables users to acquire a time-series of cervical images by looking at an on-screen timer and by acquiring individual cervical images, e.g., by pressing a button, at time intervals indicated by the on-screen timer. Typically, the on-screen timer prompts the user to acquire a cervical image every 20 seconds during a 5 minute time period, resulting in the time-series of cervical images comprising 15 cervical images.

SUMMARY OF THE INVENTION

It is desirable to automate the acquiring of such a time-series of cervical images so as to take away unnecessary load from the user. However, the inventors have found that, in cervical imaging, such automation causes users to feel less in control and/or confused. As a result, users are likely to refrain from using such an automated function.

It would be advantageous to have a system or method which is capable of automatically acquiring a time-series of cervical images while avoiding a feeling of loss of control or confusion of the user.

To better address this concern, a first aspect of the invention provides a system for acquiring cervical images, the system comprising an image acquisition subsystem for acquiring cervical images of a cervical region of a patient during a colposcopy procedure, and a display subsystem for displaying the cervical images on a display by providing image data of the cervical images to the display, wherein:

the image acquisition subsystem is arranged for, when operating in an interval mode, acquiring the cervical images at predetermined time intervals to obtain a time-series of cervical images showing changes in the cervical region over time, and reporting a progress of said acquiring to the display subsystem; and the display subsystem is arranged for establishing a progress indicator on the display by generating indicator data and providing the indicator data to the display, the progress indicator providing visual feedback on the progress of said acquiring to a user.

In a further aspect of the invention, a workstation and an imaging apparatus is provided comprising the system set forth.

In a further aspect of the invention, a method is provided for acquiring cervical images of a cervical region of a patient during a colposcopy procedure, and displaying the cervical images on a display by providing image data of the cervical images to the display, the method comprising:

acquiring the cervical images at predetermined time intervals to obtain a time-series of cervical images showing changes in the cervical region over time;

establishing a progress of said acquiring; and based on the progress, establishing a progress indicator on the display by generating indicator data and providing the indicator data to the display, the progress indicator providing visual feedback on the progress of said acquiring to a user.

In a further aspect of the invention, a computer program product is provided comprising instructions for causing a processor system to perform the method set forth.

The above measures provide a system and method for acquiring cervical images of a cervical region of a patient during a colposcopy procedure. Accordingly, a user, such as a healthcare professional, is enabled to acquire one or more cervical images during the course of the colposcopy procedure. The cervical images are then displayed on a display which may or may not be part of the system. For that purpose, image data of the cervical images is provided to the display. Accordingly, the cervical images can be displayed to the user, for example, as part of a real-time video stream showing the cervical region.

The image acquisition subsystem of the system is provided with an interval mode in which it automatically acquires the cervical images at predetermined time intervals. Accordingly, a time-series of cervical images is obtained, i.e., available to the system, which shows possible changes in the cervical region over time. Here, the term "over time" refers to a longer period of time due to a next cervical image being acquired only after expiry of a predetermined time period, as defined by a corresponding predetermined time interval, following the acquisition of a previous cervical image. The time-series of cervical images therefore shows the cervical region over a longer period of time than would otherwise be the case if the cervical images were acquired continuously by the image acquisition system. For example, the image acquisition subsystem may automatically acquire the cervical images at 20 second intervals during 5 minutes, resulting in a time-series of 15 cervical images. It is noted that, compared to a continuous video sequence, the time-series of cervical images thus needs less storage and less time by the user to view the changes in the cervical region.

The display subsystem of the system is arranged for establishing a progress indicator on the display. For that purpose, the display subsystem generates indicator data and provides the indicator to the display, thereby causing the display to display the progress indicator to the user. The progress indicator is a visual representation of the progress of the acquiring of the cervical images. Accordingly, when progress is made during the acquiring, e.g., after acquiring a next cervical image, the progress indicator is updated accordingly.

The above measures have the effect that a system and method is obtained which automatically acquire cervical images at predetermined time intervals. Accordingly, the user is not burdened anymore with having to manually acquire the cervical images over a longer period of time. As the same time, it is avoided that the user experiences a loss of control or confusion during said period by the system and method establishing a progress indicator on the display during the acquiring of the cervical images by which the user is provided with visual feedback on a status of the acquiring of the cervical images. It has been found that, by being provided with such a progress indicator, the user feels like he/she is still in control of the system and thus becomes less confused by the otherwise typically invisible functioning of the system. This is of particular importance in medical examination procedures such as colposcopy procedures since such a time-series of images is frequently acquired over a longer time period, e.g., in the case of a colposcopy procedure, over a time period of approximately 5 minutes during which the visual appearance of lesions is accentuated by the application of acetic acid solution. The progress indicator avoids that the user experiences a loss of control or confusion during said period. Advantageously, the system provides an interval mode which will be used by the users rather than ignored. Advantageously, by not being burdened with having to manually acquire the cervical images, the user can focus on observing the changes in the cervix region of the patient.

Optionally, the display subsystem is arranged for generating the indicator data to establish a timeline as the progress indicator, the timeline comprising visual symbols denoting the acquiring of respective ones of the cervical images. A timeline is a line along which events are shown in chronological order. Such a timeline is a well-suited visual representation of the progress of acquiring the cervical images in that it enables the system to intuitively show said progress by displaying the timing of the acquiring of the cervical images in relation to the progress of the acquiring. The display subsystem displays said timing by including visual symbols denoting the acquiring of respective ones of the cervical images in the timeline, e.g., by spatially distributing the visual symbols along the timeline in accordance with the predetermined time intervals. As such, the timeline provides the user with a relatively realistic indication of the timing. Moreover, by establishing the timeline as a progress indicator, the timeline is shown such that it allows the user to estimate where the system is in the process of acquiring the cervical images, i.e., how much progress has been made. Advantageously, the user is provided with an intuitive progress indicator.

Optionally, the display subsystem is arranged for generating the indicator data to indicate whether a respective one of the cervical images has or has not already been acquired. The system thus explicitly visualizes whether a respective one of the cervical images has or has not already been acquired. Advantageously, the user does not need to implicitly determine whether a respective one of the cervical images has or has not already been acquired, e.g., by estimating the present time in the timeline and determining a position of the visual symbol of a cervical image in the timeline in relation to the present time. Advantageously, the system is enabled to provide visual feedback on whether a cervical image has indeed been acquired, which may deviate from a scheduled acquisition.

Optionally, the display subsystem is arranged for using different visual symbols to indicate whether the respective one of the cervical images has or has not already been acquired. Here, the term "visual symbol" refers to a visual representation being displayed which expresses whether the respective one of the cervical images has or has not already been acquired. For example, a cervical image which is scheduled to be acquired but has not been already acquired may be denoted by a hollow circle on the timeline, whereas a cervical image which has been already acquired may be denoted by a solid circle in the timeline. Advantageously, the progress indicator provides better visual feedback to the user.

Optionally, the image acquisition subsystem is arranged for enabling the user to request acquiring of an intermediate cervical image during the acquiring of the cervical images at the predetermined time intervals. The user is thus enabled to intervene in the automatic acquiring of the cervical images by manually requesting the acquiring of an intermediate cervical image. Advantageously, the user is enabled to acquire an additional cervical image, i.e., the intermediate cervical image, if the previous cervical image which was automatically acquired by the system is deemed to be of insufficient quality or if user considers it to be otherwise desirable to acquire an intermediate cervical image. In this respect, it is noted expressions "the user acquires" and "manually acquiring" refer to the system acquiring a cervical image at the request of the user, i.e., not autonomously.

Optionally, the display subsystem is arranged for generating the indicator data to indicate the acquiring of the intermediate cervical image in the timeline. The timeline thus additionally indicates in the timeline when an intermediate cervical image was acquired. Advantageously, a complete visual representation is provided of the acquiring of cervical images, irrespective of whether they were automatically or manually acquired.

Optionally, the display subsystem is arranged for using different visual symbols to distinguish between the acquiring of the intermediate cervical image and the acquiring of the cervical images at the predetermined time intervals. For example, the intermediate cervical image may be denoted by a graphical representation of a hand indicating that said cervical image was acquired manually instead of automatically.

Optionally, the system further comprises an image quality subsystem for determining a quality of a cervical image after being acquired. The system is enabled to determine the quality of acquired cervical images. Here, the term "quality" is to be understood as referring to one or more attributes in the cervical image which determine whether or not the acquired cervical image is suitable for its intended medical purpose, i.e., for a medical diagnostic purpose or a documentation purpose. Advantageously, by being able to determine the quality of a cervical image after being acquired, the system can react to an insufficient quality, e.g., by warning the user, automatically reacquiring a cervical image, etc.

Optionally, the display subsystem is arranged for generating the indicator data to indicate the quality of a respective one of the cervical images in the timeline. The system thus explicitly visualizes the quality of at least one the acquired cervical image in the timeline. For example, the system may color-code circles representing the cervical images in the timeline, with a red color indicating a poor quality, an orange color indicating an acceptable quality, and a green color indicating a good quality. Advantageously, a complete visual representation is provided of the acquiring of cervical images, including not only the timing of the acquiring but also the quality of each of the acquired cervical images.

Optionally, the display subsystem is arranged for generating the indicator data to indicate whether the respective one of the cervical images is deemed to have an insufficient quality. It is of particular importance to the user if a cervical image is deemed to have an insufficient quality since this typically necessitates an action of the user. Such action may include manually reacquiring the cervical image, adjusting a positioning of the patient, adjusting the image acquisition subsystem, etc. The system thus explicitly visualizes whether the respective one of the cervical images is deemed to have an insufficient quality. For example, the system may display an exclamation mark next to a circle representing the cervical image in the timeline indicating that the cervical image is deemed to have an insufficient quality. Advantageously, the user can quickly react to such a situation.

Optionally, the display subsystem is arranged for recording the indicator data to enable playback of the progress indicator during playback of the time-series of cervical images. As such, the progress indicator can be displayed to the user during later playback of the time-series of cervical images. Advantageously, the user is provided not only with the cervical images, but also with a visualization of the timing of their acquisition.

Optionally, the image acquisition subsystem is arranged for enabling the user to enable and/or disable the interval mode.

It will be appreciated by those skilled in the art that two or more of the above-mentioned embodiments, implementations, and/or aspects of the invention may be combined in any way deemed useful.

Modifications and variations of the workstation, the imaging apparatus, the method, and/or the computer program product, which correspond to the described modifications and variations of the system, can be carried out by a person skilled in the art on the basis of the present description.

The invention is defined in the independent claims. Advantageously yet optional embodiments are defined in the dependent claims.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

Figure 1:
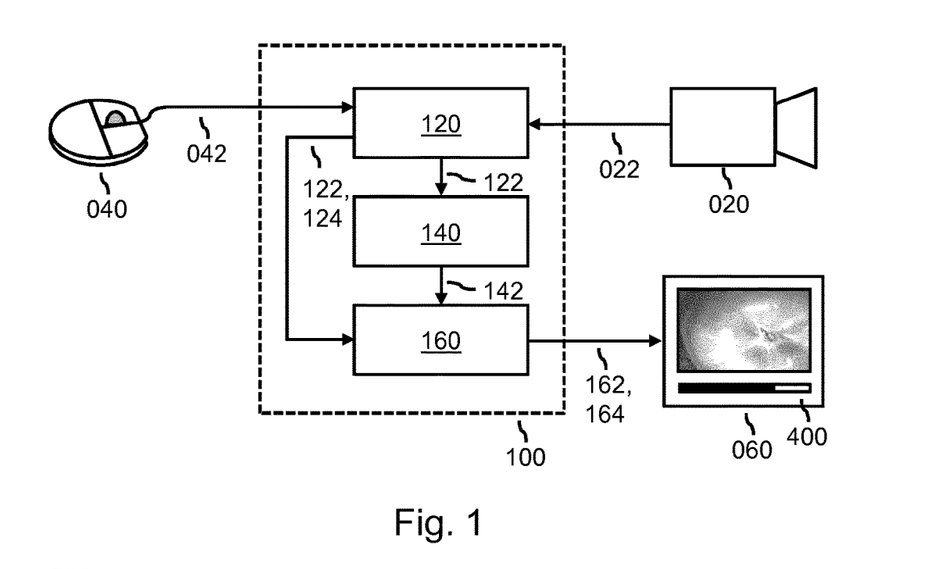
FIG. 1 shows a system for acquiring cervical images at predetermined time intervals and for providing visual feedback on the progress of said acquiring to a user.

FIG. 1 shows a system 100 for acquiring cervical images. The system 100 comprises an image acquisition subsystem 120 for acquiring cervical images 122 of a cervical region of a patient during a colposcopy procedure. In the example of FIG. 1, the image acquisition subsystem 120 is shown to acquire the cervical images 122 by receiving camera data 022 from a camera 020. FIG. 1 shows the camera 020 to be an external component, i.e., not being part of the system 100. Alternatively, the image acquisition subsystem 120 may comprise the camera 020. It is further noted that the image acquisition subsystem 120 may control the camera 020 in order to effect the acquisition of the cervical images 122, e.g., by controlling when and how the camera 020 records the cervical images.

The system 100 further comprises a display subsystem 160 for displaying the cervical images 122 on a display 060. For that purpose, the display subsystem 160 is shown to receive the cervical images 122 from the image acquisition subsystem 120. Moreover, the display subsystem 160 is shown to provide image data 162 of the cervical images 022 to the display 060. As shown in FIG. 1, the display 060 may be an external component, i.e., not being part of the system 100. Alternatively, the display subsystem 160 may comprise the display 060. By providing the image data 162 to the display 060, the display subsystem 160 may display the cervical images 122 on-screen, e.g., sequentially or simultaneously.

It is noted that the system 100 may be arranged for acquiring and subsequently displaying a real-time video stream showing the cervical region on the display 060. In this case, the camera 020 may be a video camera and the image acquisition subsystem 120 may acquire the cervical images 122 by capturing selected frames from the real-time video stream. Alternatively, the camera 020 may function as a still camera, with the image acquisition subsystem 120 effecting the recording and thus acquisition of individual cervical images.

The system 100 is further arranged to operate as follows. When operating in an interval mode, the image acquisition subsystem 120 acquires the cervical images 122 at predetermined time intervals to obtain a time-series of cervical images which shows changes in the cervical region over time. While acquiring the cervical images, the image acquisition subsystem 120 reports a progress of the acquiring to the display subsystem 160, e.g., by providing progress data 124 to the display subsystem 160. In response, the display subsystem 160 generates indicator data 164 and provides the indicator data 164 to the display 060, thereby establishing a progress indicator 400 on the display 060 which provides visual feedback on the progress of said acquiring to a user.

Figure 4:
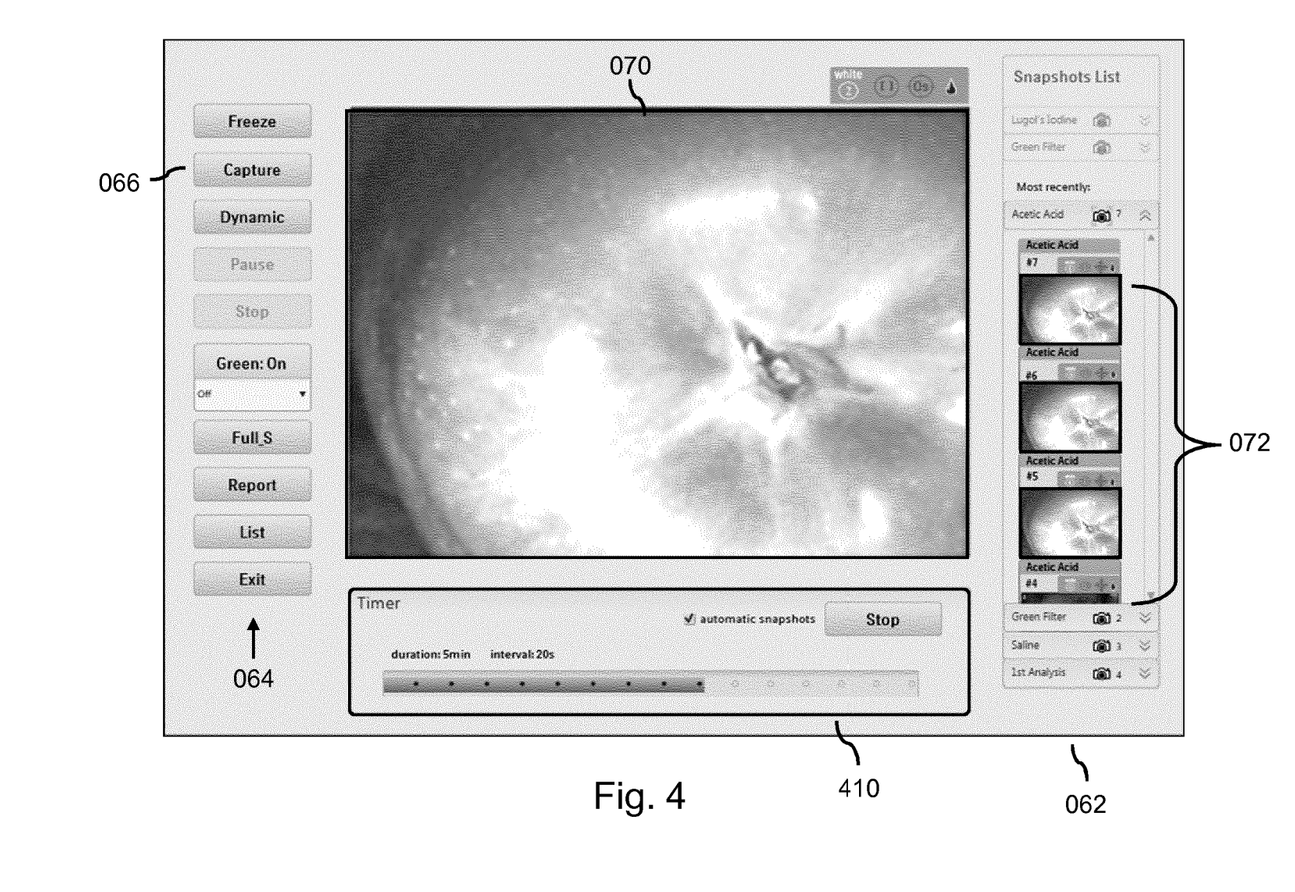
FIG. 4 shows display output of the display subsystem on the display, the display output showing acquired cervical images and a timeline as progress indicator.
Figure 5A:
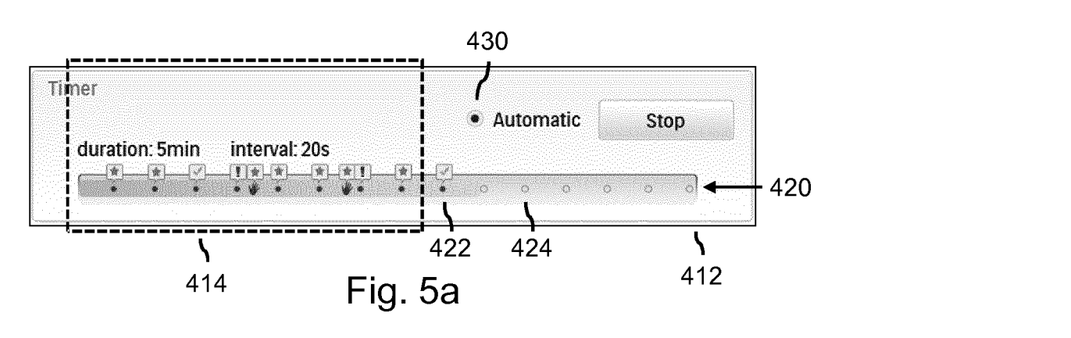
FIG. 5a shows a detailed timeline as progress indicator.
Figure 5B:
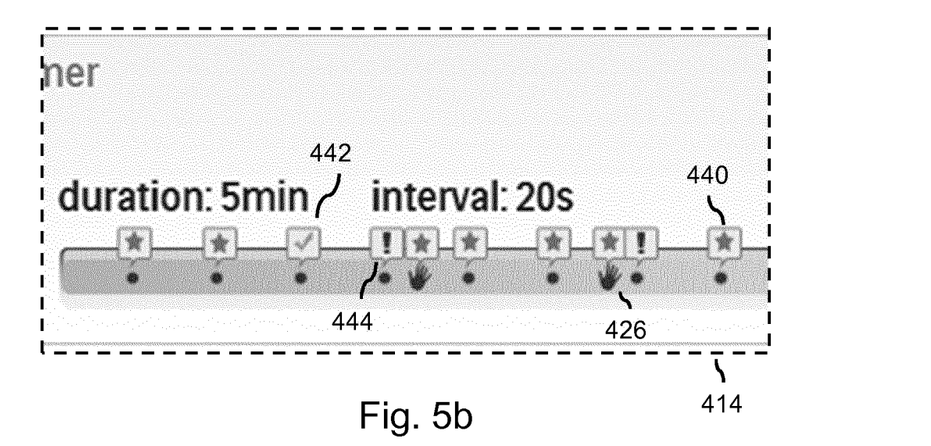
FIG. 5b provides a zoomed-in view of a part of the timeline.

FIG. 1 further shows a number of optional aspects of the present invention, such as the image acquisition subsystem 120 receiving user input data 042 from a user input device 040, and the system 100 comprising an image quality subsystem 140 for determining a quality of a cervical image after being acquired. These and other aspects will be discussed in reference to FIGS. 4, 5*a* and 5*b* showing detailed examples of the progress indicator 400.

Figure 2:
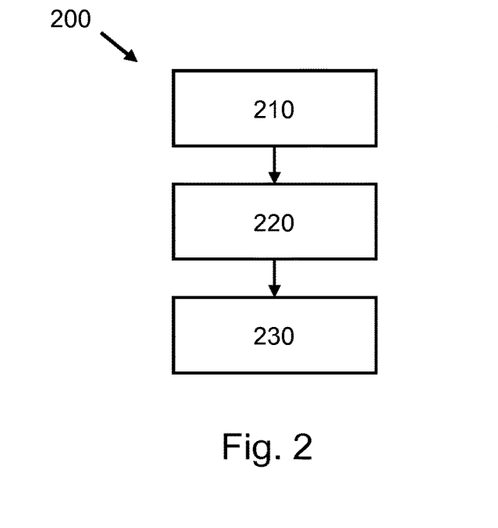
FIG. 2 shows a method for the acquiring of the cervical images and the providing of the visual feedback on the progress to the user.

FIG. 2 shows a method 200 for acquiring cervical images of a cervical region of a patient during a colposcopy procedure, and displaying the cervical images on a display by providing image data of the cervical images to the display. It is noted that the method 200 may correspond to the operation of the system 100. However, the method 200 may also be performed in separation of the system 100, e.g., on a different system or device.

The method 200 comprises, in a step titled "ACQUIRING CERVICAL IMAGES AT PREDETERMINED TIME INTERVALS", acquiring 210 the cervical images at predetermined time intervals to obtain a time-series of cervical images showing changes in the cervical region over time. The method 200 further comprises, in a step titled "ESTABLISHING PROGRESS OF ACQUIRING", establishing 220 a progress of said acquiring. The method 200 further comprises, in a step titled "ESTABLISHING PROGRESS INDICATOR ON DISPLAY", based on the progress, establishing 230 a progress indicator on the display by generating indicator data and providing the indicator data to the display, the progress indicator providing visual feedback on the progress of said acquiring to a user.

Figure 3:
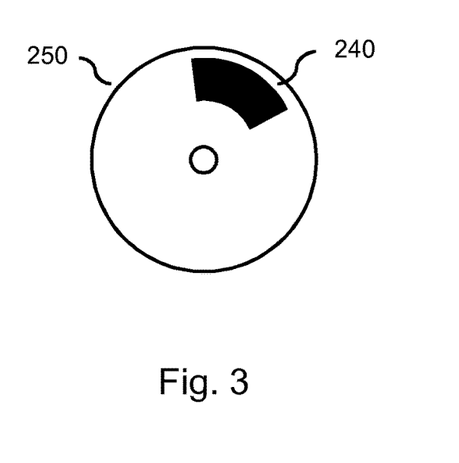
FIG. 3 shows a computer program product for implementing the method.

FIG. 3 shows a computer program product 240 comprising instructions for causing a processor system to perform the method according to the present invention. The computer program product 240 may be comprised on a computer readable medium 250, for example as a series of machine readable physical marks and/or as a series of elements having different electrical, e.g., magnetic, or optical properties or values.

An operation of the system 100 and/or method 200 may be further explained as follows. As in the above, the operation will be explained in the context of a colposcopy procedure. It will be appreciated, however, that the system 100 and/or method 200 may equally be used during any other medical examination procedure in which medical images are acquired at time intervals over a longer period of time. Accordingly, the present invention is not limited to the images being cervical images acquired during a colposcopy. Rather, the images may constitute medical images acquired during any medical examination procedure.

FIG. 4 shows an example of display output generated by the display subsystem 160 which is shown on the display 060. In particular, FIG. 4 shows a colposcopy user interface 062 which enables a user to interact with the system 100 and which enables the system 100 to provide visual feedback to the user. In order to interact with the system 100, the image acquisition subsystem 120 and/or other components of the system may be arranged for receiving user input 042 from a user input device 040 such as a computer mouse. Accordingly, the user may operate the user input device 040 to control the operation of the system 100, e.g., by selecting on-screen buttons 064 of the colposcopy user interface 062.

The colposcopy user interface 062 further shows a real-time preview 070 based on a real-time video stream obtained from the camera 020. The real-time preview 070 allows the user to check on a quality of a cervical image when acquiring the cervical image. For example, the user may check if the lighting of the cervical region is adequate, whether the cervical region is adequately framed within the real-time preview 070, etc. In this respect, it is noted that in the example of FIG. 4, the real-time preview 070 and any cervical images are shown for illustration purposes to comprise an apple rather than an actual cervical region of a patient. It will be appreciated that during actual operation of the system 100, the real-time preview 070 and any cervical images would show the actual cervical region.

FIG. 4 shows the colposcopy user interface 062 during the acquiring of the cervical images 122 at predetermined time intervals. In particular, the colposcopy user interface 062 shows a gallery 072 of the most recently acquired cervical images 122. Moreover, the colposcopy user interface 062 shows a progress indicator 410 which provides visual feedback on the progress of the acquiring to the user. In FIG. 4, the progress indicator 410 is established by the display subsystem 160 in part as a progress bar which indicates a completed part and a non-completed part of the acquiring of the cervical images 122 by means of different shading of the progress bar, i.e., dark gray versus light gray. By updating the progress indicator 410 during the acquiring, the user is provided with visual feedback on the progress. In addition, the progress indicator 410 is established in part as a timeline in that it chronologically shows when each of the cervical images 122 is scheduled to be acquired, namely by means of different visual symbols, namely solid and hollow circles, which are spatially distributed along the timeline in accordance with the predetermined time intervals. Here, a solid circle indicates that the respective one of the cervical images 122 has already been acquired by the system 100, whereas a hollow circle indicates that the respective one of the cervical images 122 has not been acquired yet. Accordingly, the progress indicator 410 provides visual feedback on the progress of the acquiring of the cervical images.

FIG. 4 further shows the image acquisition subsystem 120 being arranged for enabling the user to request acquiring of an intermediate cervical image during the acquiring of the cervical images 122 at the predetermined time intervals. In particular, the colposcopy user interface 062 is shown to provide an on-screen button 066 titled "Capture", which, when selected by the user, causes the image acquisition subsystem 120 to acquire an intermediate cervical image. The intermediate cervical image may then be included by the system in the series of cervical images, e.g., stored together with the automatically acquired cervical images. Moreover, although not shown in the example of FIG. 4 but rather in that of FIGS. 5*a* and 5*b*, the display subsystem 160 may be arranged for generating the indicator data 164 to indicate the acquiring of the intermediate cervical image in the timeline 410.

FIG. 5*a* shows a detailed timeline as progress indicator. Like the progress indicator 410 of FIG. 4, the progress indictor 412 of FIG. 5*a* chronologically shows when each of the cervical images 122 is scheduled to be acquired, namely by means of a series of circles 420 being made up of solid circles 422 and hollow circles 424. As such, the progress indicator 412 of FIG. 5*a* is provided in the form of a timeline. FIG. 5*a* further shows the progress indicator 412 displaying additional information such as "duration: 5 min" indicating that the duration of the acquiring of the cervical images is 5 minutes, and "interval: 20 s", indicating that the cervical images are acquired at 20 second intervals, thus resulting in 15 cervical images to be acquired. FIG. 5a further shows the image acquisition subsystem 120 being arranged for enabling the user to enable and disable the interval mode, namely by selecting or de-selecting an on-screen checkbox 430 labeled "Automatic".

FIG. 5b shows a zoomed-in view 414 of a part of the timeline 412 of FIG. 5a, with the corresponding part also being indicated in FIG. 5a by a dashed rectangle. The zoomed-in view 414 shows a result of the following, namely that the display subsystem 160 may be arranged for using different visual symbols to distinguish between the acquiring of the intermediate cervical image and the acquiring of the cervical images 122 at the predetermined time intervals. In the example of FIG. 5b, the display subsystem 160 denotes intermediate cervical images by means of a hand symbol 426 being displayed on the timeline at a time of their acquisition, whereas the cervical images 122 acquired at the predetermined time intervals are denoted by the solid 422 and hollow 424 circles being spatially distributed in accordance with the predetermined time intervals. Accordingly, the user is provided with visual feedback on which of the cervical images were acquired by the system 100 at the predetermined time intervals and which were acquired at the request of the user.

The zoomed-in view 414 of FIG. 5b also shows a result of the following, namely that the system 100 may comprise an image quality subsystem 140 for determining a quality of a cervical image after being acquired, and that the display subsystem 160 may be arranged for generating the indicator data 164 to indicate the quality of a respective one of the cervical images 122 in the timeline. Such an image quality subsystem 140 is also shown in FIG. 1, in which the image quality subsystem 140 is shown to receive the cervical images 122 from the image acquisition subsystem 120. Accordingly, the image quality subsystem 140 may determine the quality of each of the cervical images 122 and report the quality to the display subsystem 160, e.g., in the form of quality data 142. The display subsystem 160 may then generate the indicator data 164 to indicate the quality of each of the cervical images 122 in the time line. In particular, the display subsystem 160 may indicate whether the respective one of the cervical images is deemed to have an insufficient quality, e.g., having a quality below a threshold. FIG. 5b shows the display subsystem 160 indicating the quality of each respective one of the cervical images by means of a quality symbol placed above the circles 422, 424 and the hand symbols 426 in the timeline, with a star symbol 440 denoting a good quality, a tick symbol 442 denoting an adequate quality, and an exclamation mark 444 denoting a poor or insufficient quality. However, the visual indication of the quality may also take a different form, such as a color-coding of the circles and hand symbols.

In general, the visual symbols in the timeline which denote already acquired ones of the cervical images 122 may be selectable by the user. In particular, the display subsystem 160 may be arranged for displaying an acquired cervical image in response to the user selecting a corresponding visual symbol in the timeline. For example, the user may operate the user input device 040, e.g., a computer mouse and thereby an on-screen cursor, to select any one of the visual symbols shown in the timeline 410 of the user interface 062.

Moreover, in general, the image acquisition subsystem 120 may be arranged for automatically detecting changes in the cervical region, such as acetowhite or vascular changes such as their onsets. The display subsystem 160 may further be arranged for indicating such changes in the timeline 410. For example, the display subsystem 160 may display a circular icon in the timeline 410 denoting that acetowhite changes have been detected at that particular time, and/or an icon with red branches denoting that vascular changes have been detected at that particular time. The image acquisition subsystem 120 may further be arranged for automatically acquiring an intermediate cervical image upon detecting such changes, and the display subsystem 160 may be arranged for indicating the acquiring of such an intermediate cervical image in the timeline, e.g., using the aforementioned circular icon for acetowhite changes and the icon with red branches for vascular changes. In order to automatically detect the changes in the cervical region, the image acquisition subsystem 120 may make use of detection techniques as are known per se, e.g., from the PCT Patent Publication WO/2012/123881. In particular, the image acquisition subsystem 120 may use the therein described techniques of calculating an acetowhite kinetic score and/or an acetowhite margin score in order to detect and quantify acetowhite occurrence and to derive acetowhite changes from said scores. Additionally or alternatively, the image acquisition subsystem 120 may use the therein described technique of calculating a vascular pattern score to determine vascular changes. It will be appreciated, however, that the image acquisition subsystem 120 may equally use other techniques to detecting changes in the cervical region such as the aforementioned acetowhite or vascular changes.

The image quality subsystem 140 may determine the quality of a cervical image in various ways, for example by determining a presence or absence of at least one of following attributes in the cervical image: motion blur, region-of-interest out of focus, too low a magnification factor, an area of a tissue being imaged is obscured from view by a natural fluid, an area of the tissue is obscured from view by a foreign object, specular reflection, inadequate cleaning of the tissue, insufficient coverage of the tissue by a chemical agent applied to the tissue for improving visualization of an abnormal area of the tissue.

Motion blur is the apparent streaking of a rapidly moving object in a still image or a sequence of images such as in a video. Motion blur is caused by changes in the scene being captured during the capturing, due to a rapid relative movement of the camera 020 and the scene to be captured, or due to a too long exposure time per single image frame with respect to the rate of relative movements within the scene. As known from the technical field of image processing, motion blur may be detected by, e.g., analysis of the frequency spectrum to determine whether there is a loss of high frequencies. The analysis may be implemented using a high-pass filter. Alternatively, motion estimation techniques may be used, such as three-dimensional recursive search (3DRS) motion estimation or optical flow estimation, all of which are known from the technical field of motion estimation.

If a region-of-interest in the cervical image is out of focus, fewer details are present in the image than in case the region-of-interest is in focus. The out-of-focus condition may be detected by, e.g., analysis of the frequency spectrum to determine whether there is a loss of high frequencies, e.g., by using a high-pass filter. In order to detect the region-of-interest, the image quality subsystem 140 may use a region-of-interest detection technique, e.g., to detect the transformation zone or other areas of tissue in the cervical image.

If the magnification factor used by the camera of the medical imaging system not being high enough, this typically results in insufficiency of detail in the cervical image, which may be detected by the image quality subsystem 140 as follows. First, a characterizing portion of the cervical region under inspection may be identified so as to enable to determine the location and/or orientation of the camera 020 relative to the cervical region. In colposcopy, the cervix may serve as the characterizing portion. In order to identify the cervix in the cervical image, the image quality subsystem 140 may make use of techniques such as template matching, contour tracing or machine learning. The apparent size of the cervix may then be determined relative to the size of the overall cervical image. If the cervix appears rather small compared the image size, a magnification has been used that may be too low.

If an area of the tissue to be captured in the images is covered by, e.g., blood or mucus, the area is obscured from view. Bleeding or the secretion of mucus may be detected by, e.g., color analysis and/or movement of the fluid relative to tissue or relative to the camera. For example, the color of blood generally differs from the color of the tissue.

The presence of a foreign object in the images may be detected based on, e.g., size, shape, and/or color. The size and shape may be determined by tracing the coherent movement of pixels associated with the foreign object when the foreign object enters the viewport of the camera 020 due to relative movement of the camera and the foreign object.

Specular reflection may occur if the light from a light source which illuminates the cervical region is strongly reflected by the surface of the tissue into the camera 020. Specular reflection causes so-termed clipping artifacts which may be detected using techniques as known from the technical fields of image processing and image analysis.

Inadequate cleaning may be detected as a result of detecting bleeding and/or as a result of glare and/or as a result of an abnormal color or a texture of an abnormal material on the tissue's surface, which can themselves be detected as exemplified above.

The attribute "insufficient coverage of the tissue by a chemical agent applied to the tissue for improving visualization of an abnormal area of the tissue" may be determined as follows. First, the region-of-interest, e.g., a transformation zone, is identified in the cervical images 122. Then, the cervical images 122 are analyzed to determine whether or not there is a difference between the appearance of the region-of-interest in the cervical images 122 before applying the chemical agent and the appearance of the region-of-interest in the images just after applying the chemical agent. If the region-of-interest has been covered adequately, the appearance of the region-of-interest after applying the chemical agent should have a uniform character. If the appearance is not uniform, his may be an indication that part of the region-of interest has not been covered adequately or not at all.

Figure 6:
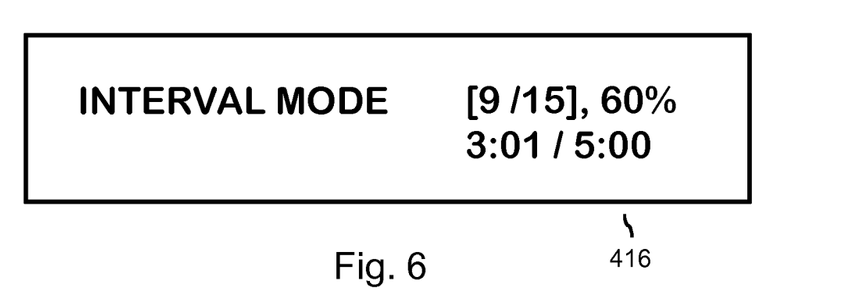
FIG. 6 shows another form of progress indicator.

FIG. 6 shows another example of a progress indicator 416 as established by the display subsystem 160. Here, the progress indicator 416 is shown to be text-based rather than being constituted by a timeline and/or progress bar. In particular, the progress indicator 416 is shown to indicate the progress of the acquiring of the cervical images 122 by indicating how many cervical images have already been acquired out of the total number of cervical images which are scheduled to be acquired, namely "[9/15]" denoting that 9 cervical images have already been acquired out of a total of 15. In addition, the progress indicator 416 shows the progress in the form of a percentage, namely "60%", and in the form of an elapsed time in relation to a total time, namely 3:01 minutes being elapsed out of a total of 5:00 minutes.

It will be appreciated that the progress indicator 400-416 is not limited to the forms shown in FIGS. 4-6 but rather may take any suitable form which provides visual feedback on the progress of the acquiring of the cervical images 122 to a user.

In general, the display subsystem 160 may be arranged for recording the indicator data 164 to enable playback of the progress indicator 400-416 during playback of the time-series of cervical images 122. For that purpose, the indicator data 164 may be stored in association with the cervical images 122. Moreover, the display subsystem 160 may be arranged for playing back the cervical images 122 and the progress indicator. As such, the display subsystem 160 may enable the user to review the cervical images 122.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for providing interactive guidance for acquiring cervical images, the system comprising a computer system comprising one or more processors programmed with computer program instructions that, when executed, cause the computer system to:
periodically acquire, via a camera, when operating in an interval mode, cervical images at predetermined time intervals to obtain a scheduled acquisition of a time-series of cervical images showing changes in a cervical region over time during a colposcopy procedure;
monitor a progress of the scheduled acquisition during the colposcopy procedure;
cause a timeline component indicating the progress of the scheduled acquisition to be presented on a user interface during the colposcopy procedure, the timeline component comprising:
one or more symbols, wherein
one or more first ones of the symbols are located at one or more first positions on the timeline component to indicate one or more first times at which one or more first cervical images were acquired; and
one or more second ones of the symbols are located at one or more second positions on the timeline component to indicate one or more second times at which one or more second cervical images are to be acquired, the one or more second ones of the symbols being different than the one or more first ones of the symbols;
wherein the one or more symbols comprise one or more of hollow circles, solid circles, star symbols, tick symbols, check symbols, or hand symbols, and wherein
the one or more first ones of the symbols comprise a solid circle indicating an acquired cervical image, and
the one or more second symbols comprise a hollow circle indicating a cervical image to be acquired; and
a progress bar component at a given position on the timeline component between one of the one or more first symbols and one of the one or more second symbols;
cause, based on the progress monitoring, the one or more second symbols to be updated on the user interface, as the one or more second cervical images are respectively acquired, to indicate that the one or more second cervical images have been acquired; and
cause the progress bar component to be continuously updated to indicate a completed part and/or non completed part of the scheduled acquisition.

2. The system according to claim 1, wherein the one or more first symbols are visually different from the one or more second symbols.

3. The system according to claim 1, wherein the one or more processors are configured to enable user to request acquiring of one or more intermediate cervical images during the colposcopy procedure between the scheduled acquisition of consecutive ones of the cervical images.

4. The system according to claim 3, wherein the one or more processors are configured to cause presentation of one or more third ones of the symbols located at one or more third positions on the timeline component during the colposcopy procedure to indicate one or more third times at which the one or more intermediate cervical images were acquired.

5. The system according to claim 4, wherein the one or more third symbols are visually different from the one or more first and second symbols.

6. The system according to claim 1, wherein the one or more processors are configured to determine a quality of a cervical image after being acquired.

7. The system according to claim 6, wherein the timeline component comprises indicator data that indicates the quality of a respective one of the cervical images.

8. The system according to claim 7, wherein the indicator data indicates whether the respective one of the cervical images is deemed to have an insufficient quality.

9. The system according to claim 1, wherein the one or more processors are configured to enable user to enable and/or disable the interval mode.

10. A workstation or imaging apparatus comprising the system of claim 1.

11. A method for providing interactive guidance for acquiring cervical images of a cervical region of a patient during a colposcopy procedure, the method comprising:
periodically acquiring, via a camera, when operating in an interval mode, cervical images at predetermined time intervals to obtain a scheduled acquisition of a time-series of cervical images showing changes in the cervical region over time during the colposcopy procedure;
monitoring, with one or more processors, a progress of the scheduled acquisition during the colposcopy procedure;
causing, with one or more processors, a timeline component indicating the progress of the scheduled acquisition to be presented on a user interface during the colposcopy procedure, the timeline component comprising:
one or more symbols, wherein
one or more first ones of the symbols are located at one or more first positions on the timeline component to indicate one or more first times at which one or more first cervical images were acquired;
one or more second ones of the symbols are located at one or more second positions on the timeline component to indicate one or more second times at which one or more second cervical images are to be acquired, the one or more second ones of the symbols being different than the one or more first ones of the symbols; and
wherein the one or more symbols comprise one or more of hollow circles, solid circles, star symbols, tick symbols, check symbols, or hand symbols, and wherein the one or more first ones of the symbols comprise a solid circle indicating an acquired cervical image, and the one or more second symbols comprise a hollow circle indicating a cervical image to be acquired; and a progress bar component at a given position on the timeline component between one of the one or more first symbols and one of the one or more second symbols;

causing, with one or more processors, based on the progress monitoring, the one or more second symbols to be updated on the user interface, as the one or more second cervical images are respectively acquired, to indicate that the one or more second cervical images have been acquired; and causing, with one or more processors, the progress bar component to be continuously updated to indicate a completed and/or non completed part of the scheduled acquisition.

12. A tangible, non-transitory, machine-readable media storing instructions that, when executed by one or more physical processors, effectuate operations comprising:

periodically acquiring, via a camera, when operating in an interval mode, cervical images at predetermined time intervals to obtain a scheduled acquisition of a time-series of cervical images showing changes in cervical region over time during a colposcopy procedure;

monitoring, with one or more processors, a progress of the scheduled acquisition during the colposcopy procedure;

causing, with one or more processors, a timeline component indicating the progress of the scheduled acquisition to be presented on a user interface during the colposcopy procedure, the timeline component comprising:

one or more symbols, wherein:

one or more first ones of the symbols are located at one or more first positions on the timeline component to indicate one or more first times at which one or more first cervical images were acquired;

one or more second ones of the symbols are located at one or more second positions on the timeline component to indicate one or more second times at which one or more second cervical images are to be acquired, the one or more second ones of the symbols being different than the one or more first ones of the symbols; and wherein the one or more symbols comprise one or more of hollow circles, solid circles, star symbols, tick symbols, check symbols, or hand symbols, and wherein the one or more first ones of the symbols comprise a solid circle indicating an acquired cervical image, and the one or more second symbols comprise a hollow circle indicating a cervical image to be acquired; and a progress bar component at a given position on the timeline component between one of the one or more first symbols and one of the one or more second symbols;

causing, with one or more processors, based on the progress monitoring, the one or more second symbols to be updated on the user interface, as the one or more second cervical images are respectively acquired, to indicate that the one or more second cervical images have been acquired; and causing, with one or more processors, the progress bar component to be continuously updated to indicate a completed and/or non completed part of the scheduled acquisition.

* * * * *